United States Patent
Nakamoto et al.

(10) Patent No.: US 11,845,926 B2
(45) Date of Patent: Dec. 19, 2023

(54) KLEBSIELLA PNEUMONIAE STRAIN INDUCING INFLAMMATION IN LIVER

(71) Applicant: KEIO UNIVERSITY, Tokyo (JP)

(72) Inventors: Nobuhiro Nakamoto, Tokyo (JP); Nobuo Sasaki, Tokyo (JP); Ryo Aoki, Tokyo (JP); Kentaro Miyamoto, Tokyo (JP); Toshiro Sato, Tokyo (JP); Takanori Kanai, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 142 days.

(21) Appl. No.: 17/130,570

(22) Filed: Dec. 22, 2020

(65) Prior Publication Data

US 2021/0123109 A1 Apr. 29, 2021

Related U.S. Application Data

(63) Continuation of application No. 16/389,454, filed on Apr. 19, 2019, now abandoned.

(30) Foreign Application Priority Data

Apr. 23, 2018 (JP) .................................. 2018-082192

(51) Int. Cl.
| | | |
|---|---|---|
| C12R 1/22 | (2006.01) | |
| C12R 1/37 | (2006.01) | |
| C12R 1/46 | (2006.01) | |
| C12N 1/20 | (2006.01) | |
| A01K 67/027 | (2006.01) | |

(52) U.S. Cl.
CPC ............ *C12N 1/205* (2021.05); *A01K 67/027* (2013.01); *C12N 1/20* (2013.01); *A01K 2227/105* (2013.01); *A01K 2267/0387* (2013.01); *C12R 2001/22* (2021.05); *C12R 2001/37* (2021.05); *C12R 2001/46* (2021.05)

(58) Field of Classification Search
None
See application file for complete search history.

(56) References Cited

PUBLICATIONS

Sabino, Joao, et al., "Primary sclerosing cholangitis is characterised by intestinal dysbiosis independent from IBD", Gut, vol. 65, pp. 1681-1689 (2016) (in English; cited in specification).

Kummen, Martin, et al., The gut microbial profile in patients with primary sclerosing cholangitis is distinct from patients with ulcerative colitis without biliary disease and healthy controls, Gut, vol. 66, pp. 611-619 (2017) (in English; cited in specification).

Iwasawa, K., et al., "Characterisation of the faecal microbiota in Japanese patients with paediatric-onset primary sclerosing cholangitis", Gut, vol. 66, pp. 1344-1346 (2017) (in English; cited in specification).

Doud, M. S., et al., "A k2A-positive Klebsiella pneumoniae causes liver and brain abscess in a Saint Kitt's man", International Journal of Medical Sciences, vol. 6, pp. 301-304 (2009) (in English; U.S. Appl. No. 16/389,454).

(Continued)

*Primary Examiner* — S. Devi

(74) *Attorney, Agent, or Firm* — WHDA, LLP

(57) ABSTRACT

To identify a microorganism causing the development of primary sclerosing cholangitis associated with ulcerative colitis. A *Klebsiella pneumoniae* strain inducing inflammation in the liver.

5 Claims, 10 Drawing Sheets
(9 of 10 Drawing Sheet(s) Filed in Color)

(56) References Cited

PUBLICATIONS

Nakamoto, N. et al., "Integrated collaboration of intestinal microbiota induces bacterial translocation and Th17 immune response in primary sclerosing cholangitis", Hepatology, vol. 66, No. 1, Suppl. AASLD Abstracts, p. 445A, abstract #832, Oct. 20-24, 2017 (in English; U.S. Appl. No. 16/389,454).

Fang, C.T., et al., "Klebsiella pneumoniae Genotype K1: An Emerging Pathogen That Causes Septic Ocular or Central Nervous System Complications from Pyogenic Liver Abscess", Clinical Infectious Diseases., vol. 45, Aug. 1, 2007, pp. 284-293 (in English; U.S. Appl. No. 16/389,454).

Non-Final Office Action dated Nov. 3, 2022, issued in U.S. Appl. No. 17/130,557. (11 pages).

Office Action dated Feb. 28, 2023, issued in counterpart JP application No. 2019-080978, with English translation. (10 pages).

Fang, et al., "A Novel Virulence Gene in Klebsiella pneumoniae Strains Causing Primary Liver Abscess and Septic Metastatic Complications", J. Exp. Med., 2004, vol. 199, No. 5, pp. 697-705, cited in JP Office Action dated Feb. 28, 2023. (10 pages).

Sarris, et al., "Distribution of the putative type VI secretion system core genes in *Klebsiella* spp.", Infection, Genetics and Evolution, 2011, vol. 11, pp. 157-166, cited in JP Office Action dated Feb. 28, 2023. (11 pages).

Pollheimer, et al., "Will we ever model PSC?—It's hard to be a PSC model!", Clinics and Research in Hepatology and Gastroenterology, 2011, vol. 35, pp. 792-804, cited in JP Office Action dated Feb. 28, 2023. (14 pages).

Fickert, et al., "A New Xenobiotic-Induced Mouse Model of Sclerosing Cholangitis and Biliary Fibrosis", The American Journal of Pathology, 2007, vol. 171, No. 2, pp. 525-536, cited in JP Office Action dated Feb. 28, 2023. (13 pages).

Final Office Action dated Feb. 28, 2023, issued in U.S. Appl. No. 17/130,557. (8 pages).

Office Action dated Jul. 18, 2023, issued in counterpart JP application No. 2019-080978, with English translation. (4 pages).

Fig. 2a Liver
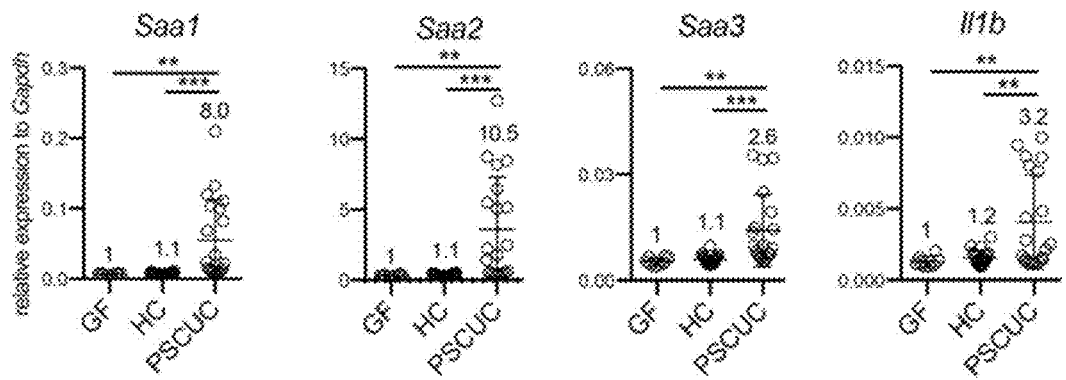
Fig. 2b Colon
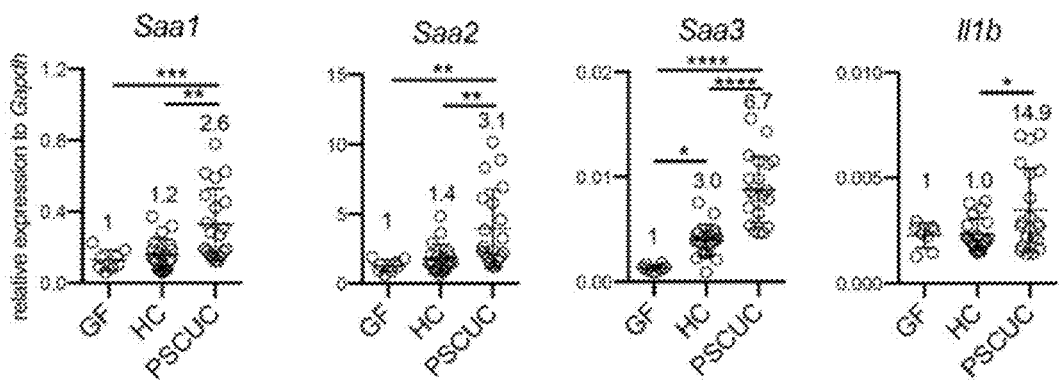
Fig. 2c Spleen
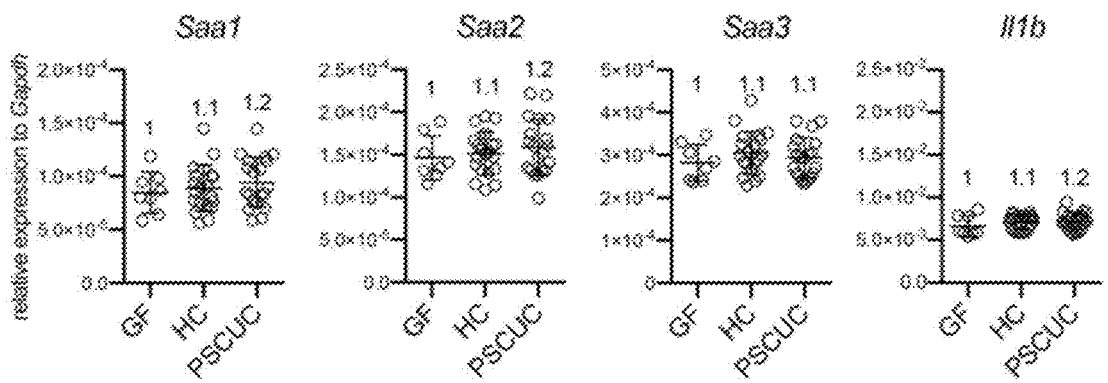

KLEBSIELLA PNEUMONIAE STRAIN INDUCING INFLAMMATION IN LIVER

CROSS-REFERENCE TO RELATED APPLICATIONS

This application is a continuation of U.S. application Ser. No. 16/389,454 (abandoned) filed on Apr. 19, 2019, which in turn claims priority from Japanese Application No. 2018-082192 filed on Apr. 23, 2018. The entirety of each of these related applications is hereby incorporated by reference.

BACKGROUND OF THE INVENTION

Field of the Invention

The present invention relates to a *Klebsiella pneumoniae* strain inducing inflammation in the liver.

Description of the Related Art

Primary sclerosing cholangitis (PSC) is an idiopathic chronic cholestatic chronic liver disease and causes end-stage hepatic cirrhosis through the progression of biliary stricture and collapse of the biliary tree. To date, no definitive treatment other than liver transplantation for this symptom has been established, and a further understanding of the pathophysiology is needed for treating this incurable disease.

Since portal bacteremia and high-level endotoxin in cholangiocytes have been observed in patients with primary sclerosing cholangitis, it is considered that bacterial translocation, in which intestinal bacterial flora passes through the damaged intestinal barrier, plays an important role in liver inflammation. However, regardless of the presence of many evidences of bacterial translocation in patients with primary sclerosing cholangitis, the mechanisms that trigger collapse of intestinal barrier and bacterial translocation are still unknown.

It is known that more than half of the patients with primary sclerosing cholangitis suffer from ulcerative colitis, and it is suggested that the bacterial translocation induced by chronic colitis has a risk of causing hepatitis. In contrast, only a very small number of patients with ulcerative colitis have primary sclerosing cholangitis. Furthermore, the ulcerative colitis patients having primary sclerosing cholangitis exhibit discontinuous segmental colitis (right sided colitis). This is remarkably contrast to continuous rectal lesions in typical ulcerative colitis not complicated with primary sclerosing cholangitis. Accordingly, only having colitis as the underlying disease is insufficient for the onset of primary sclerosing cholangitis complicated with ulcerative colitis, and it is considered that other disease factors are involved in the onset.

In recent years, microbial analysis has reported that the intestinal bacterial flora of ulcerative colitis patients having primary sclerosing cholangitis is different from those of healthy subjects and typical ulcerative colitis patients not having primary sclerosing cholangitis (Non-Patent Literatures 1 to 3). Considering the difference in clinical symptoms of ulcerative colitis complicated with primary sclerosing cholangitis and typical ulcerative colitis not complicated with primary sclerosing cholangitis, it is suggested that abnormality in the intestinal bacterial flora (dysbiosis) may play an important role in the development of primary sclerosing cholangitis associated with ulcerative colitis.

CITATION LIST

Non-Patent Literature

Non-Patent Literature 1

Sabino, J., et al., Primary sclerosing cholangitis is characterised by intestinal dysbiosis independent from IBD, Gut 65, 1681-1689, (2016)

Non-Patent Literature 2

Kummen, M., et al., The gut microbial profile in patients with primary sclerosing cholangitis is distinct from patients with ulcerative colitis without biliary disease and healthy controls, Gut 66, 611-619, (2017)

Non-Patent Literature 3

Iwasawa, K., et al., Characterisation of the faecal microbiota in Japanese patients with paediatric-onset primary sclerosing cholangitis, Gut 66, 1344-1346, (2017)

However, there is not yet clear evidence showing that dysbiosis causes the development of primary sclerosing cholangitis associated with ulcerative colitis, and it is also unclear whether a certain microbial species contributes to the development of primary sclerosing cholangitis associated with ulcerative colitis. Accordingly, there is a strong demand for identification of a microorganism that causes the development of primary sclerosing cholangitis associated with ulcerative colitis.

SUMMARY OF THE INVENTION

The present inventors have intensively studied in view of the above problems and, as a result, have identified a *Klebsiella pneumoniae* strain, a *Proteus mirabilis* strain, and an *Enterococcus gallinarum* strain that cause the development of primary sclerosing cholangitis associated with ulcerative colitis, and the present invention has been accomplished.

That is, the present invention, for example, relates to the following [1] to [14]:

[1] A *Klebsiella pneumoniae* strain inducing inflammation in the liver;

[2] The *Klebsiella pneumoniae* strain according to [1], inducing a Th17 cell in the liver;

[3] The *Klebsiella pneumoniae* strain according to [1] or [2], having an ability to form a pore on the large intestinal epithelium;

[4] The *Klebsiella pneumoniae* strain according to any one of [1] to [3], having a type 6 secretion system;

[5] The *Klebsiella pneumoniae* strain according to any one of [1] to [4], derived from a patient suffering from both primary sclerosing cholangitis and ulcerative colitis;

[6] The *Klebsiella pneumoniae* strain according to any one of [1] to [5], comprising a DNA consisting of the nucleotide sequence registered in the National Center for Biotechnology Information (NCBI) under Assembly Name: ASM385182v1;

[7] The *Klebsiella pneumoniae* strain according to any one of [1] to [6], whose deposit number is NITE BP-02879;

[8] The *Klebsiella pneumoniae* strain according to any one of [1] to [5], comprising a DNA consisting of the nucleotide sequence registered in the National Center for Biotechnology Information (NCBI) under Assembly Name: ASM386511v1;

[9] A *Proteus mirabilis* strain whose accession number is NITE BP-02923;

[10] An *Enterococcus gallinarum* strain whose accession number is NITE BP-02922;

[11] Use of the *Klebsiella pneumoniae* strain according to any one of [1] to [8] for prediction or diagnosis of the development of primary sclerosing cholangitis;

[12] Use of the *Klebsiella pneumoniae* strain according to any one of [1] to [8], a *Proteus mirabilis* strain, and an *Enterococcus gallinarum* strain for prediction or diagnosis of the development of primary sclerosing cholangitis;

[13] The use for prediction or diagnosis of the development of primary sclerosing cholangitis according to [12], wherein the *Proteus mirabilis* strain is one whose accession number is NITE BP-02923; and the *Enterococcus gallinarum* strain is one whose accession number is NITE BP-02922; and

[14] A method for producing a mouse model suffering from both primary sclerosing cholangitis and ulcerative colitis, the method comprising:

administering a bacterial solution containing the *Klebsiella pneumoniae* strain according to any one of [1] to [8] to a mouse; and administering 3,5-dicarbetoxy-1,4-dihydrocollidine to a mouse, and The *Klebsiella pneumoniae* KP-P1 strain having the accession number NITE BP-02879 has been deposited at the NITE Patent Microorganisms Depositary on Feb. 8, 2019, and the *Proteus mirabilis* strain having the accession number NITE BP-02923, and the *Enterococcus gallinarum* strain having the accession number NITE BP-02922 have been deposited at the NITE Patent Microorganisms Depositary on Mar. 20, 2019 under the terms of the Budapest treaty. The depository is NITE Patent Microorganisms Depository, National Institute of Technology and Evaluation (NITE), #122, 2-5-8 Kazusakamatari, Kisarazu-shi, Chiba 292-0818, Japan.

According to the present invention, a *Klebsiella pneumoniae* strain, a *Proteus mirabilis* strain, and an *Enterococcus gallinarum* strain can be used for prediction of the development of primary sclerosing cholangitis. In addition, a mouse model suffering from both primary sclerosing cholangitis and ulcerative colitis can be used for establishing a method for treating primary sclerosing cholangitis.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

FIGS. 2a to 2c are graphs showing the results of measurement of gene expression levels of serum amyloid protein A (Saa 1 to 3) and IL-1 (Il1b) in the livers (2A), colons (2B), and spleens (2C) of GF mice (GF), humanized gnotobiotic mice administered a fecal sample of a healthy subject (HC), and humanized gnotobiotic mice administered a fecal sample of a patient suffering from both primary sclerosing cholangitis and ulcerative colitis (PSCUC). *: P<0.05, : P<0.01, *: P<0.001, ****: P<0.0001 (The same applies to the following figures);

DETAILED DESCRIPTION OF THE PREFERRED EMBODIMENTS

Figure 1A:
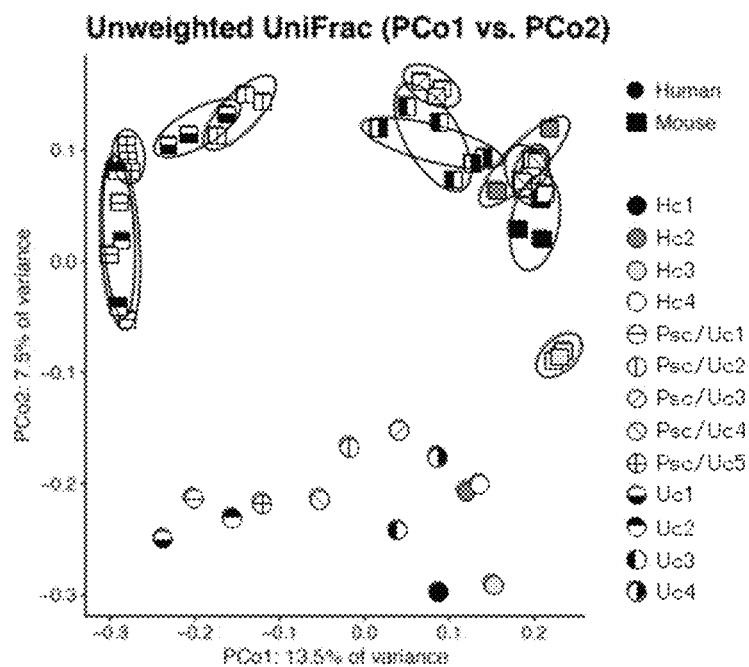
FIG. 1a is a graph showing the results of unweighted UniFrac analysis of bacterial flora present in fecal samples of healthy subjects (Hc 1 to 4), patients suffering from both primary sclerosing cholangitis and ulcerative colitis (Psc/Uc 1 to 5), and patients suffering from ulcerative colitis only (Uc 1 to 4) and in fecal samples of humanized gnotobiotic mice administered the fecal samples of these patients.

Embodiments of the present invention will now be described with reference to the drawings, but the scope of the present invention is not limited to the disclosed embodiments.

The present invention will now be described in detail.

<Klebsiella pneumoniae Strain>

An aspect of the present invention relates to a *Klebsiella pneumoniae* strain inducing inflammation in the liver. The inflammation of livers includes not only inflammation of livers but also inflammation of intra- and extra-hepatic bile ducts, and examples thereof include hepatitis and cholangitis. Examples of hepatitis include viral hepatitis, drug-induced hepatitis, alcoholic hepatitis, non-alcoholic steatohepatitis, and autoimmune hepatitis. Examples of cholangitis include sclerosing cholangitis (such as primary sclerosing cholangitis, IgG4-related sclerosing cholangitis, and secondary sclerosing cholangitis), primary biliary cholangitis (primary biliary cirrhosis), ascending cholangitis, secondary sclerosing cholangitis, and recurrent pyogenic cholangitis.

The *Klebsiella pneumoniae* strain of the present invention is preferably a strain inducing Th17 cells in the liver. The induction of Th17 cells can be verified by, for example, treating mononuclear cells of the liver with a fluorescence labeled anti-CD4 antibody and an anti-IL-17 antibody and verifying a significant increase in IL-17-producing CD4 positive helper T (Th17) cells by flow cytometric analysis.

The *Klebsiella pneumoniae* strain of the present invention preferably has the ability to form pores which is capable of forming pores on the large intestinal epithelia. The pores may have any shape and size allowing enteric bacteria to leak through the pores. For example, the diameter may be 0.1 to 20 μm, more preferably 0.5 to 15 μm, in observation of large intestinal epithelium with a scanning electron microscope. The leakage of enteric bacteria through the pores can be verified by, for example, hybridizing the DNA of the enteric bacteria with a fluorescent probe, staining the large intestinal epithelial cells with a fluorescent dye that emits fluorescence having a color different from that of the fluorescence of the probe, and observing the section of the large intestinal epithelium with a fluorescence microscope. Although the details of the mechanism of forming pores are unclear, it is inferred that the *Klebsiella pneumoniae* strain of the present invention comes into direct contact with large intestinal epithelium to induce apoptosis, resulting in the formation of pores.

The *Klebsiella pneumoniae* strain of the present invention preferably has a type 6 secretion system (T6SS). The type 6 secretion system can be verified by, for example, the presence of a gene in comparative analysis of whole genome sequencing of the strain.

The *Klebsiella pneumoniae* strain of the present invention is preferably derived from a patient suffering from both primary sclerosing cholangitis and ulcerative colitis described below. The strain can be isolated from a fecal sample of the patient by a known method using a generic growth medium. Examples of the medium include a brain heart infusion (BHI) medium, a MacConkey agar medium, and a VRBG medium.

The *Klebsiella pneumoniae* strain of the present invention preferably has a DNA consisting of the nucleotide sequence registered in the National Center for Biotechnology Information (NCBI) under Assembly Name: ASM385182v1, and the *Klebsiella pneumoniae* strain is more preferably one whose deposit number is NITE BP-02879.

The *Klebsiella pneumoniae* strain of the present invention preferably has a DNA consisting of the nucleotide sequence registered in the National Center for Biotechnology Information (NCBI) under Assembly Name: ASM386511v1.

<Primary Sclerosing Cholangitis>

Primary sclerosing cholangitis can be diagnosed in accordance with known clinical guidelines. For example, as the diagnosis items, when "bile duct image" (A) and "increase in alkaline phosphatase level" (B) are defined as major items; "complication of inflammatory bowel disease" (a) and "liver tissue image (fibrous cholangitis/onion skin lesion)" (b) are defined as minor items; and the bile duct image (A) is classified into "recognition of findings of bile duct image characteristic to primary sclerosing cholangitis" (A1) and "no recognition of findings of bile duct image characteristic to primary sclerosing cholangitis" (A2), only definite diagnosis and probable diagnosis in the following Table 1 can be treated as primary sclerosing cholangitis.

TABLE 1

| Major item | | | Minor item | | |
|---|---|---|---|---|---|
| (A1) | (A2) | (B) | (a) | (b) | Diagnosis |
| ○ | — | ○ | — | — | Definite diagnosis |
| ○ | — | — | ○ | — | Definite diagnosis |
| ○ | — | — | — | ○ | Definite diagnosis |
| — | ○ | ○ | ○ | ○ | Definite diagnosis |
| ○ | — | — | — | — | Probable diagnosis |
| — | ○ | ○ | ○ | — | Probable diagnosis |
| — | ○ | ○ | — | ○ | Probable diagnosis |
| — | ○ | — | ○ | ○ | Probable diagnosis |
| — | ○ | — | ○ | — | Possible diagnosis |
| — | ○ | — | — | ○ | Possible diagnosis |

The alkaline phosphatase level can be measured by a known method. For example, it can be measured in accordance with the common standard method proposed by the Japan Society of Clinical Chemistry (JSCC). When the measured value is, for example, 2 to 3 times as high as the reference value, the value can be determined as an abnormal value.

The bile duct image can be judged to be (A1) or (A2) mentioned above based on, for example, findings of diffuse wall irregularities and strictures associated with inflammation of intra- and extra-hepatic bile ducts characteristic to primary sclerosing cholangitis by performing an endoscopic retrograde cholangiography (ERC) or magnetic resonance cholangiopancreatography (MRCP) test.

The above-mentioned diagnosis of primary sclerosing cholangitis needs to exclude malignant tumors such as cholangiocarcinoma, IgG4-related sclerosing cholangitis, and secondary sclerosing cholangitis. The IgG4-related sclerosing cholangitis can be diagnosed based on, for example, combination of four criteria ((1) finding of characteristic bile duct image, (2) increase in serum IgG4 level, (3) complication of IgG4-related disease of an organ other than biliary tract, and (4) characteristic histopathological findings) in Clinical diagnostic criteria of IgG4-related sclerosing cholangitis, 2012 (Journal of Hepato-Biliary-Pancreatic Sciences, vol. 19, pp. 536-542).

Examples of the secondary sclerosing cholangitis include congenital diseases, such as Caroli's disease and cystic fibrosis; chronic obstructive diseases, such as choledocholith, biliary stricture, Mirizzi syndrome, anastomotic stenosis after liver transplantation, and tumors; infectious diseases, such as bacterial cholangitis, recurrent pyogenic cholangitis, parasitic infection, and cytomegalovirus infection; poisoning diseases, such as erroneous intrabiliary injection of alcohol, formaldehyde, or hypertonic saline; immune abnormalities, such as eosinophilic cholangitis and those with AIDS; ischemic diseases, such as those related to vascular injury, post-traumatic sclerosing cholangitis, hepatic artery embolism after liver transplantation, rejection after liver transplantation, or coronary arterial anticancer drug infusion; and invasive lesions, such as systemic vasculitis, amyloidosis, sarcoidosis, systemic mastocytosis, eosinophilia, Hodgkin's disease, and xanthogranulomatous cholangitis.

<Ulcerative Colitis>

Ulcerative colitis can be diagnosed in accordance with known clinical guidelines. For example, ulcerative colitis can be clearly diagnosed when the following item (B-1) or (B-2) is satisfied, in addition to the items (A) and (C), and the diseases (D) are excluded.

(A) Clinical symptom: Persistent or recurrent mucous or bloody stool or medical history thereof is observed.

(B-1) Endoscopic examination: (1) The mucous membrane is diffusely affected, the visible vascular pattern disappears, and coarse or fine granular form is observed. Furthermore, friability and hemorrhage-prone properties (contact bleeding) cause attachment of mucous and bloody purulent secretion; or (2) multiple erosion, ulcer, or pseudopolyposis is observed. (3) In general, lesions are observed continuously from the rectum.

(B-2) Enema X-ray examination: (1) Diffuse change like a coarse or fine granular form of the surface of the mucosal membrane, (2) multiple erosion or ulcer, and (3) pseudopolyposis are observed. In addition, disappearance of *Haustra coli* (lead pipe appearance) or narrowing or shortening of the intestine is observed.

(C) Biopsy histologic examination: In the active phase, diffuse inflammatory cell infiltration, cryptic tumor, and a severe decrease in goblet cells are observed in the entire mucosal layer. Since all of them are nonspecific findings, comprehensive judgment is performed. In the remission phase, abnormal arrangement of glands (meander, bifurcation) and atrophy remain. These changes are generally observed continuously from the rectum to the oral side.

(D) Infectious enteritis, such as bacterial and *Clostridium difficile* enteritis, amebic colitis, *Salmonella* enteritis, *Campylobacter* enteritis, colonic tuberculosis, and *Chlamydia* enteritis; Crohn's disease; radiation irradiated colitis; drug-induced colitis; lymphoid follicular hyperplasia; ischemic colitis; intestinal Behcet, and so on.

In addition to the above definite diagnosis cases, when the items (B-1) or (B-2) and (C) are satisfied multiple times, ulcerative colitis can be clearly diagnosed when findings grossly and histologically characteristic to ulcerative colitis are observed by excision surgery or autopsy.

<Use for Prediction of Development of Primary Sclerosing Cholangitis>

Another aspect of the present invention relates to use of the *Klebsiella pneumoniae* strain only or use of the *Klebsiella pneumoniae* strain, a *Proteus mirabilis* strain, and an *Enterococcus gallinarum* strain for predicting the development of primary sclerosing cholangitis.

As described above, for example, a *Klebsiella pneumoniae* strain derived from a patient suffering from both primary sclerosing cholangitis and ulcerative colitis is characterized by (1) having a type 6 secretion system, (2) having an ability to form a pore on large intestinal epithelia, and (3) inducing Th17 cells in the liver. This suggests that in a patient suffering from ulcerative colitis, the *Klebsiella pneumoniae* strain having a type 6 secretion system forms pores on the large intestinal epithelium to leak enteric bacteria, such as a *Proteus mirabilis* strain and an *Enterococcus gallinarum* strain, and induce Th17 cells in the liver, resulting in complication of primary sclerosing cholangitis.

Accordingly, if genome sequencing has revealed that the *Klebsiella pneumoniae* strain in a fecal sample of a patient suffering from ulcerative colitis has a type 6 secretion system, the development of primary sclerosing cholangitis can be predicted. In addition, if formation of pores is recognized on the large intestinal epithelium when a biopsy tissue sample of the large intestine is subsequently observed with a scanning electron microscope, the prediction accuracy is increased. Furthermore, if an increase in Th17 cells in the liver is recognized in, for example, flow cytometry of a biopsy sample of the liver, the prediction accuracy is further increased.

In addition, a fecal sample of a patient is cultured, and the presence or absence of a *Proteus mirabilis* strain or an *Enterococcus gallinarum* strain, in addition to the *Klebsiella pneumoniae* strain, can be used as a predictor. The *Proteus mirabilis* strain is preferably a *Proteus mirabilis* strain whose accession number is NITE BP-02923 and the *Enterococcus gallinarum* strain is preferably an *Enterococcus gallinarum* strain whose accession number is NITE BP-02922.

<Method for Producing Mouse Model Suffering from Both Primary Sclerosing Cholangitis and Ulcerative Colitis>

Another aspect of the present invention relates to a method for producing a mouse model suffering from both primary sclerosing cholangitis and ulcerative colitis. Specifically, the method for producing a mouse model suffering from both primary sclerosing cholangitis and ulcerative colitis includes a step of administering a bacterial solution containing the *Klebsiella pneumoniae* strain described in the paragraph <*Klebsiella pneumoniae* strain> described above to a mouse and a step of administering 3,5-dicarbetoxy-1,4-dihydrocollidine to a mouse. Although the step of administering a bacterial solution containing the *Klebsiella pneumoniae* strain to a mouse and the step of administering 3,5-dicarbetoxy-1,4-dihydrocollidine to a mouse may be performed in any order, it is preferred to perform the step of administering a bacterial solution containing the *Klebsiella pneumoniae* strain to a mouse and then administering 3,5-dicarbetoxy-1,4-dihydrocollidine to the mouse.

Although the original mouse to be used for producing the mouse model may be any mouse that can suffer from both primary sclerosing cholangitis and ulcerative colitis, a germ-free mouse is preferred. Examples of the germ-free mouse include mice produced from strains such as BALB/c, C57BL/6, and ICR.

In order to produce the mouse model, for example, a suspension is prepared by suspending fecal samples collected from primary sclerosing cholangitis and ulcerative colitis patients in, for example, a phosphate-buffered saline (PBS) solution, and the suspension is orally administered to original mice to produce humanized gnotobiotic mice.

Subsequently, the humanized gnotobiotic mice 19 to 23 days after the administration can be given free access to a diet containing 0.01% to 0.1% 3,5-dicarbetoxy-1,4-dihydrocollidine (DDC) for 12 to 16 days to produce a mouse model suffering from both primary sclerosing cholangitis and ulcerative colitis.

Another aspect of the present invention relates to the *Proteus mirabilis* strain whose accession number is NITE BP-02923.

Another aspect of the present invention relates to the *Enterococcus gallinarum* strain whose accession number is NITE BP-02922.

Although the embodiments of the present invention have been described in detail, they are merely examples, and the present invention is not limited thereto. The scope of the present invention should be interpreted by the claims and includes all modifications within the meaning and scope equivalent to the claims.

EXAMPLES

The present invention will now be further specifically described based on Examples, but is not limited to these Examples.

[Example 1] Comparison of Intestinal Bacterial Floras of Human and Humanized Gnotobiotic Mouse (1) Collection of Fecal Sample Subjects were 14 patients suffering from both primary sclerosing cholangitis and ulcerative colitis (hereinafter referred to as "Psc/Uc" in some cases), 8 patients suffering from ulcerative colitis only (hereinafter referred to as "Uc" in some cases), and 10 healthy subjects (hereinafter referred to as "Hc" in some cases). Primary sclerosing cholangitis was diagnosed based on clinical guidelines and findings by cholangiography and liver biopsy. Ulcerative colitis was diagnosed by combination of endoscopic examination, histopathologic examination, and radiographic and serological examinations. Fecal samples were collected using feces collection tubes and were suspended in a solution containing 40% glycerol and an equivalent amount (w/v) of PBS, and the resulting suspensions were rapidly frozen and were stored at −80° C. until use.

(2) Production of Humanized Gnotobiotic Mouse

The frozen stock of each fecal sample of the above (1) was thawed and suspended in 6 volumes of PBS, and the suspension was passed through a 70-μm cell strainer to prepare a suspension for oral administration. 200 μL of the suspension for oral administration was orally administered to 6 to 8-week old male germ-free mice (GF mice, available from Sankyo Laboratories) using a stainless steel oral gavage needle to produce humanized gnotobiotic mice. Fecal samples were collected from the humanized gnotobiotic mice 3 to 4 weeks after the administration.

(3) Collection of DNA in Fecal Sample

DNAs of the bacteria in the human fecal samples in the above (1) and the humanized gnotobiotic mice fecal samples in the above (2) were isolated by an enzymatic dissolution method using lysozyme (manufactured by Sigma-Aldrich Co. LLC) and achromopeptidase (manufactured by FUJIFILM Wako Pure Chemical Corporation). The resulting DNA samples were treated with Ribonuclease A (manufactured by FUJIFILM Wako Pure Chemical Corporation) for purification and were then precipitated with 20% polyethylene glycol solution (PEG 6000, 2.5 M sodium chloride aqueous solution). Each precipitate was collected by centrifugation and was then washed with 75% ethanol and dissolved in a Tris-EDTA buffer.

(4) 16S rRNA Metagenomic Analysis

Figure 1B:
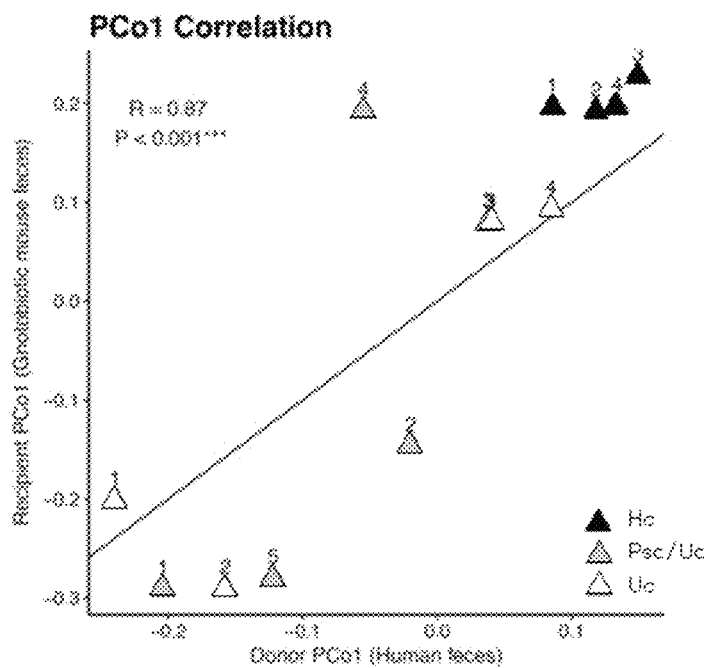
FIG. 1b is a graph showing the results of principal coordinates analysis based on the UniFrac analysis of the human fecal samples and the humanized gnotobiotic mouse fecal samples.

The hypervariable region V3-V4 of 16S rRNA gene of each of the DNAs obtained in the above (3) was amplified with TaKaRa Ex Taq (R) Hot Start Version (manufactured by Takara Bio Inc.), and the amplicon was purified with AMPure XP (manufactured by Beckman Coulter, Inc.). A mixture sample was prepared from the resulting DNA, and sequencing was performed with Miseq Reagent Kit V3 and Miseq Sequencer (manufactured by Illumina, Inc.) in accordance with the product manual. The sequence analysis was performed with QIIME software package ver. 1.9.1. Paired-end sequences were joined using a fastq-join tool in the EA-Utils software package. From the quality filter-passed sequences, 15,000 high-quality sequences were chosen for each sample. Chimera sequences were detected by the USEARCH, and the primer sequences were removed using cutadapt. Assignment of OTUs was performed using the UCLUST algorism with a sequence similarity of 96%. The assignment of OTUs was performed using the GLSEARCH program by similarity searching against the 16S (RDP version 10.27 and CORE update 2 Sep. 2012) and the NCBI genome database. The data were rarefied to 10,000 sequences per sample, as determined by the rarefaction curves, and the relative abundances of the bacteria were determined. The unweighted UniFrac analysis was performed in accordance with the method described in the document (Tsuda, A., et al., Influence of Proton-Pump Inhibitors on the Luminal Microbiota in the Gastrointestinal Tract, Clin. Transl. Gastroenterol., 6, e89 (2015)). The results are shown in FIGS. 1a and 1b. The results demonstrated that the main bacterial flora was conserved in human and humanized gnotobiotic mice.

[Example 2] Measurement of Gene Expression Levels of Serum Amyloid Protein a (SAA) and IL-1R in Organ The liver, colon, and spleen of the humanized gnotobiotic mouse produced in Example 1 were homogenized, and total RNA of each organ was extracted using RNeasy Mini Kit (manufactured by QIAGEN N.V.). Complementary DNA was synthesized from 1 μg of the resulting total RNA by reverse transcription, and each target gene was amplified by PCR using AmpliTaq Gold Fast PCR MasterMix (manufactured by Applied Biosystems, Inc.) and the following designed primers (manufactured by Thermo Fisher Scientific Inc.).

Glyceraldehyde-3-phosphate dehydrogenase (Gapdh): Mm03302249 g1
  Saa1: Mm00656927_g1
  Saa2: Mm04208126_mH
  Saa3: Mm00441203 m1
  IL-1β: Mm01336189_g1

The amplicons were quantitatively measured by real-time PCR using TaqMan Universal Master Mix and StepOne Plus systems (manufactured by Applied Biosystems, Inc.). In each sample, the target gene expression level was standardized using Gapdh. The results are shown in FIGS. 2a to 2c. The results demonstrated that in the liver (FIG. 2a) and the colon (FIG. 2b) of humanized gnotobiotic mice (PSCUC in the graphs) administered a fecal sample derived from Psc/Uc, the gene expression of serum amyloid protein A and IL-1β was increased and that bacteria involved in hepatic and large intestinal diseases were present in the intestinal bacterial flora of Psc/Uc.

Figure 3A:
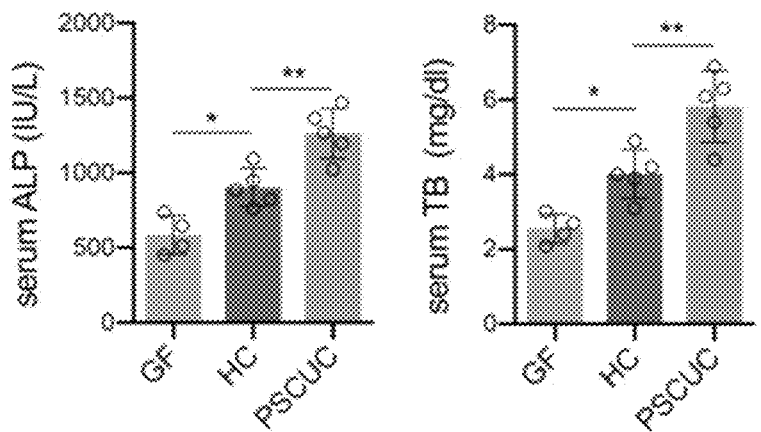
FIG. 3a includes graphs showing the results of measurement of serum alkaline phosphatase (ALP, left) and serum total bilirubin (TB, right) of GF, HC, and PSCUC.

[Example 3] Production of Mouse Model Suffering from Both Primary Sclerosing Cholangitis and Ulcerative Colitis (1) Measurement of Serum Alkaline Phosphatase and Serum Total Bilirubin GF mice and the humanized gnotobiotic mice produced in Example 1 (2) by orally administering feces of Hc or Psc/Uc 21 days after the administration were given free access to a diet containing 0.05% 3,5-dicarbetoxy-1,4-dihydrocollidine (DDC) for 14 days, and serum alkaline phosphatase (ALP) and total bilirubin (TB) were measured by an LDH-UV kinetic method (manufactured by SRL, Inc.). The results are shown in FIG. 3a. The humanized gnotobiotic mice administered the fecal sample derived from Psc/Uc (PSCUC in the graphs) showed high expression levels of both ALP (left in FIG. 1a) and TB (right in FIG. 1a), compared to those in GF mice (GF in the graphs) and the humanized gnotobiotic mice administered the fecal sample derived from Hc (HC in the graphs).

(2) Histochemical Observation of Liver

Figure 3B:
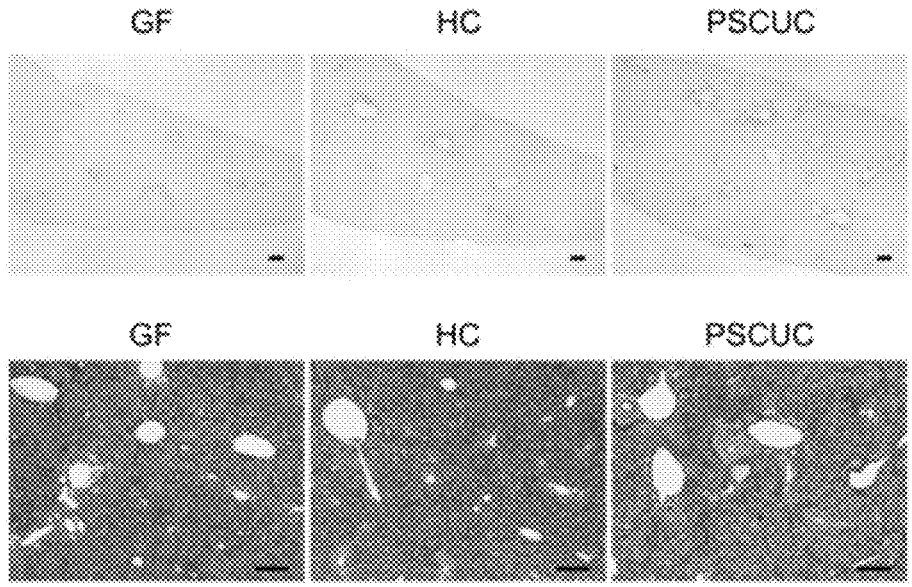
FIG. 3b includes photomicrographs of samples of specimens prepared by Sirius red staining (above) and hematoxylin-eosin staining and Masson-trichrome staining (below) of liver tissue sections of GF, HC, and PSCUC. The scale bars indicate 100 μm.

Livers were collected from the DDC-treated humanized gnotobiotic mice and were fixed in 10% formalin and embedded in paraffin according to a usual method to produce paraffin blocks. Sections were cut from the paraffin blocks and were stained with hematoxylin-eosin and Masson-trichrome or stained with Sirius red to prepare specimen samples. The results of microscopic observation of the specimen samples are shown in FIG. 3b. The upper part of FIG. 3b shows the results of Sirius red staining, and the lower part of FIG. 3b shows the results of co-staining with hematoxylin-eosin and Masson-trichrome. In the liver of the humanized gnotobiotic mice administered the fecal sample derived from Psc/Uc, hepatic disorder due to fiber formation in the liver was observed.

(3) Immunological Analysis

Livers were collected from the DCC-treated mice and were perfused with PBS from the portal vein. After the perfusion, the livers were chopped and passed through a 100-μm nylon mesh to obtain cells of the livers.

The resulting cells were suspended in 40% Percoll solution and then overlaid in 75% Percoll fraction, followed by density gradient centrifugal separation at 840×g for 20 minutes at room temperature. Mononuclear cells were collected from the intermediate layer. The resulting mononuclear cells were washed and were suspended in FACS buffer. The mononuclear cells were subjected to blocking treatment using an anti-Fc antibody (CD16/32, manufactured by BD Pharmingen) and were then subjected to intracellular staining with an anti-CD4 antibody (APC-cy7, BV510) and an anti-CD11b antibody (APC-cy7). The intracellular stained cells were treated with Ionomycine (500 ng/mL) or Golgistop (10 μg/mL, manufactured by BD Biosciences) in the presence of lipopolysaccharide (derived from *Escherichia coli* B5, manufactured by Sigma-Aldrich Co. LLC) or PMA (50 ng/mL, manufactured by Sigma-Aldrich Co. LLC) and brefeldin A (10 μg/mL, manufactured by BD Biosciences).

Figure 3C:
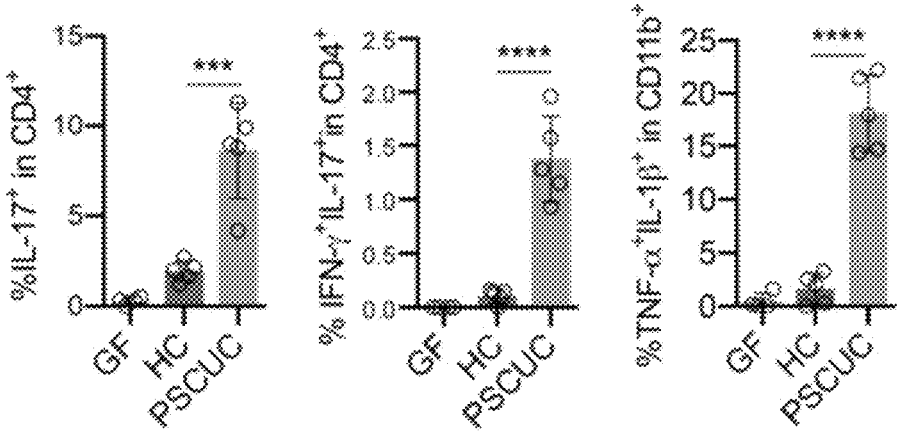
FIG. 3c includes graphs showing the results of flow cytometric analysis of the cells in the livers of GF, HC, and PSCUC.

Subsequently, an anti-IFN-γ antibody, an anti-TNF-α antibody, an anti-IL-1 antibody, and an anti-IL-17 antibody (manufactured by BD Pharmingen) were added thereto, followed by co-culture at 4° C. for 20 minutes. The cells after the culture were washed with PBS and were measured with a cell sorter ("FACS CantoII," manufactured by Becton, Dickinson and Company) and analyzed using FlowJo software (manufactured by Tree Star, Inc.). The results are shown in FIG. 3c. The results demonstrated that in DDC-treated mice administered a fecal sample derived from Psc/Uc, the development of hepatic disorder and recruitment of Th17 cells and IL-1B+CD11b$^+$ macrophages were observed, and a mouse model suffering from both primary sclerosing cholangitis and ulcerative colitis was provided.

[Example 4] Identification of Intestinal Bacterial Flora Derived from Psc/Uc (1) Analysis of Intestinal Bacterial Flora in Mouse Fecal Sample In order to identify the bacteria that induce hepatitis, the livers, mesenteric lymph nodes, and spleens were collected from humanized gnotobiotic mice orally administered a fecal sample of Hc or Psc/Uc and SPF mice (6- to 8-week old C57BL/6 mice, available from CLEA Japan, Inc.) as a control group on the 21st day from the administration, and the bacteria were cultured on agar plates. As a result, no colonies were observed in the liver and spleen of any of the mice. In the mesenteric lymph nodes, colonies were observed in only that from the humanized gnotobiotic mice administered a fecal sample derived from Psc/Uc. Bacterial flora analysis of 16S rRNA of the colonies demonstrated that the bacteria of the colonies were *Klebsiella pneumoniae* (KP), *Proteus mirabilis* (PM), and *Enterococcus gallinarum* (EG).

(2) Analysis of Intestinal Bacterial Flora in Human Fecal Sample

Figure 4A:
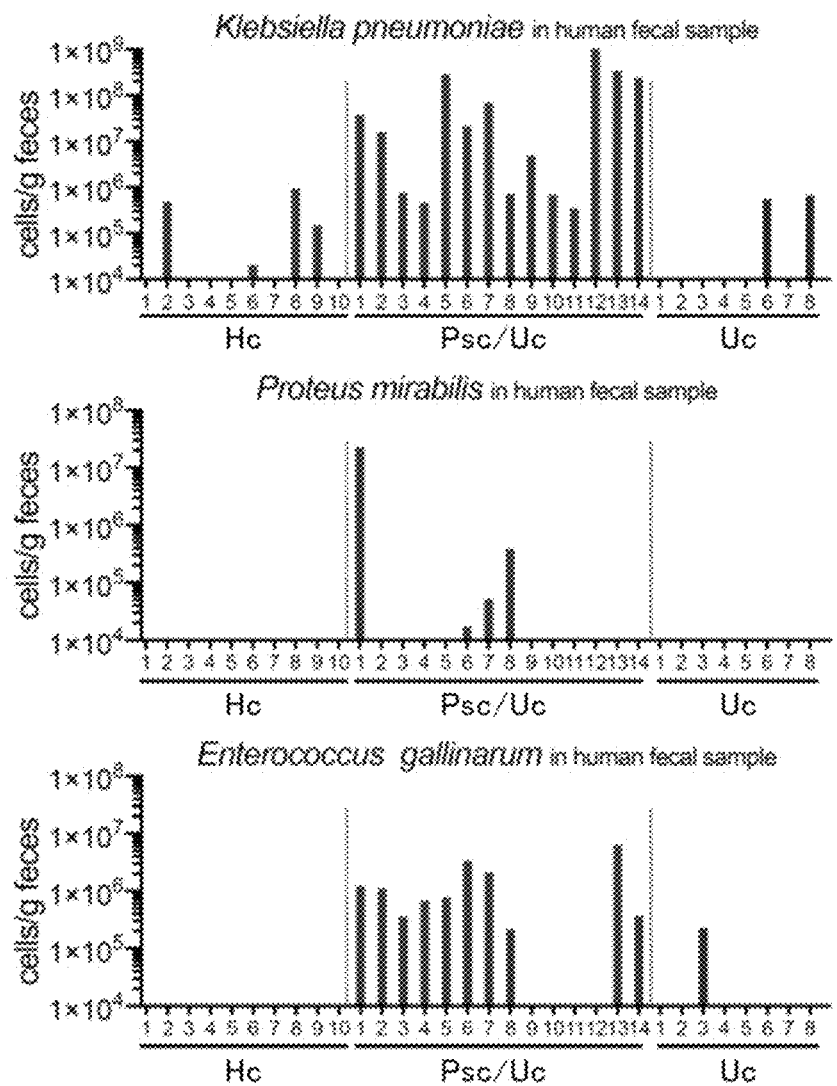
FIG. 4a includes graphs showing the results of counting the cell number of the *Klebsiella pneumoniae* (KP), *Proteus mirabilis* (PM), and *Enterococcus gallinarum* (EG) contained in fecal samples of Hc, Psc/Uc, and Uc.

Fecal samples derived from Hc, Psc/Uc, and Uc were anaerobically cultured in BHI medium (manufactured by Becton, Dickinson and Company), and the KP, PM, and EG cells were counted. The results are shown in FIG. 4a. It was demonstrated that in the fecal sample derived from Psc/Uc, KP was remarkably present, and PM and EG were also present. The KP included a KP-P1 strain (deposit number: NITE BP-02879) having a DNA consisting of the nucleotide sequence registered in the National Center for Biotechnology Information (NCBI) under Assembly Name: ASM385182v1 and a KP strain having a DNA consisting of the nucleotide sequence registered in the National Center for Biotechnology Information (NCBI) under Assembly Name: ASM386511v1. The PM included a strain whose accession number is NITE BP-02923, and the EG included a strain whose accession number is NITE BP-02922.

Figure 4B:
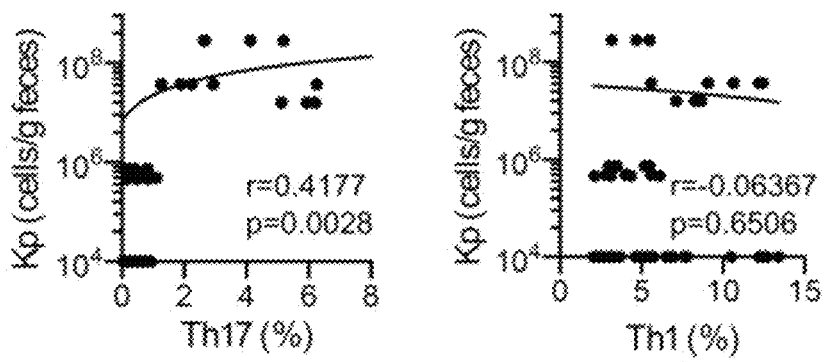
FIG. 4b includes graphs showing correlations between the proportion of Th17 cells or Th1 cells in the liver of PSCUC and the number of *Klebsiella pneumoniae* cells in the fecal samples thereof.

(3) Correlation Analysis of KP in Fecal Samples of Human and Humanized Gnotobiotic Mice As in Example 2 (3), correlations between the proportion of Th17 cells or Th1 cells in the liver of the humanized gnotobiotic mice administered the fecal sample derived from Psc/Uc and the number of KP cells in the fecal sample were verified by flow cytometric analysis using an anti-CD3e antibody (FITC), an anti-CD4 antibody (APC-cy7, BV510), an anti-IFN-γ antibody, and an anti-IL-17 antibody, and the significance was verified by a Spearman rank-order correlation test. The results are shown in FIG. 4b. A correlation was found between KP and Th17 cells (left in FIG. 4b), but no correlation was found between KP and Th1 cells (right in FIG. 4b). The results demonstrated that KP derived from Psc/Uc contributed to induction of Th17 cells in the liver.

Figure 5A:
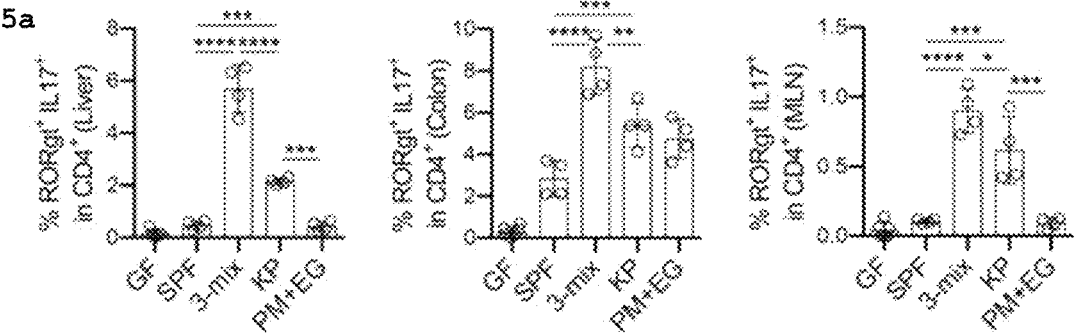
FIG. 5a includes graphs showing the results of flow cytometric analysis of the cells in the livers, colons, and mesenteric lymph nodes of humanized gnotobiotic mice administered KP only (KP), PM and EG (PM+EG), and three strains of KP, PM, and EG (3-mix), respectively, in fecal samples derived from Psc/Uc, GF mice (GF), and SPF mice (SPF).

[Example 5] Evaluation of Properties of KP, PM, and EG (1) Evaluation of Induction of Th17 Cell in Liver by Single Strain and Mixed Strain Administration In order to investigate contribution of the above-mentioned three strains to Th17 cell induction, $1\times10^8$ CFU/200 µL of KP, PM, and EG were orally administered to GF mice by (1) KP alone (KP), (2) combination of PM and EG (PM+EG), or (3) combination of three strains (3-mix) each twice per week. On the 21st day from the administration, as in Example 2 (3), the liver, colon, and mesenteric lymph node were analyzed by flow cytometry using an anti-CD4 antibody (APC-cy7, BV510), an anti-IL-17 antibody, and an anti-RORγt antibody (manufactured by BD Pharmingen). The results are shown in FIG. 5a. In all organs of the liver (left in FIG. 5a), the colon (center in FIG. 5a), and the mesenteric lymph node (right in FIG. 5a), Th17 cell induction was recognized in the KP administration groups, in particular, in the 3-mix administration group, compared to those in GF mice (GF) and SPF mice (SPF) not administered the strains.

(2) Histochemical Observation of Large Intestine

Ileum tissues including fecal materials of humanized gnotobiotic mice prepared by administering KP alone, PM and EG, and three strains of KP, PM, and EG to GF mice (KP, PM+EG gnoto, and 3-mix gnoto) were fixed in Carnoy's solution for 3 hours and embedded in paraffin to produce paraffin blocks. Tissue sections were cut from the blocks and were hybridized at 50° C. overnight using EUB338 probe (ALEXA555 label), hybridizing with the DNA of the above-mentioned strains, prepared such that the final concentration in hybridization buffer (20 mM Tris-HCl (pH 7.4), 0.9 M NaCl, 0.1% SDS, 20% formamide) was 10 µg/mL.

Figure 5B:
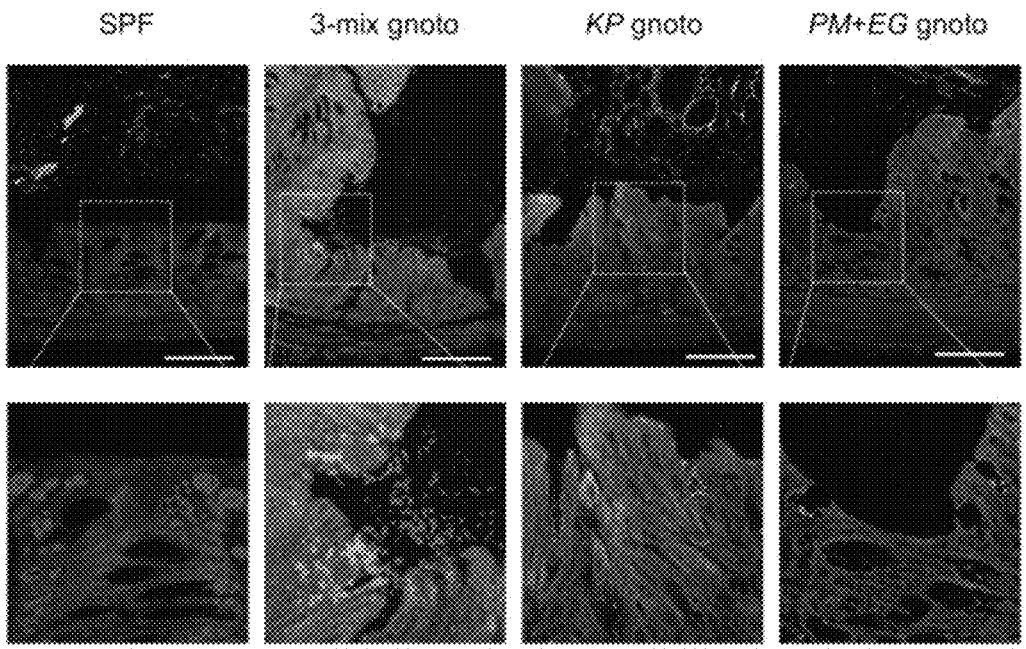
FIG. 5b includes fluorescence micrographs of the ilea of the SPF mouse and the humanized gnotobiotic mice (KP gnoto, PM+EG gnoto, and 3-mix gnoto). The scale bars indicate 50 μm.

The tissue sections were washed with washing buffer (20 mM Tris-HCl (pH 7.4), 0.9 M NaCl) for 10 minutes and with PBS for 10 minutes three times and were then stained with Phalloidin-iFluor (manufactured by Abcam plc.). After washing with PBS for 10 minutes three times, the sections were mounted in Prolong anti-fade mounting media with DAPI (manufactured by Life Technologies). Microscopic observation was performed with a BIO-REVO BZ-9000 fluorescence microscope (manufactured by Keyence Corporation). The results are shown in FIG. 5b. It was observed that the bacteria stained in red in the micrographs invaded the large intestine epithelium mucous membrane in the 3-mix gnoto and KP gnoto, and some of the bacteria further invaded the large intestinal epithelium. In particular, the invasion was remarkable in the 3-mix gnoto. In contrast, the invasion was only slight in the PM+EG gnoto and was not observed in the control SPF.

[Example 6] Evaluation 1 of Ability to Form Pore on Large Intestinal Epithelium of KP Stain (1) Production of Monolayer Organoid Co-Culture System Healthy human colon organoids were embedded in Matrigel (Corning) and were three-dimensionally cultured in Advanced DMEM/F12 culture solution (containing penicillin/streptomycin, 10 mM HEPES, 2 mM GlutaMAX, 1×B27 (manufactured by Life Technologies), 1 mM N-acetylcysteine (manufactured by FUJIFILM Wako Pure Chemical Corporation), 10 nM Gastrin I (manufactured by Sigma-Aldrich Co. LLC), 50 ng/mL human recombinant EGF, 0.5 µM A83-01, 3 µM SB202190, 50% Afamin-Wnt3a (Afm-W) complex condition medium (CM, v/v), R-spondin 1 (R)-CM (10% v/v), and Noggin (N)-CM (10% v/v)).

The three-dimensionally cultured human colon organoids were cultured for at least one day in a medium containing 10 µM Y-27632 and containing Afm-Wnt, R-spondin 1, Noggin, EGF, A83-01, and SB202190 and were then separated and seeded in a ThinCert 24-well plate (manufactured by Greiner Bio-One International GmbH) coated with 10% Cellmatrix type I-C (manufactured by Nitta Gelatin Inc.) and having a pore size of 0.4 µm. 2 to 3 days after the seeding, the medium was replaced by a condition medium not containing Afm-Wnt and SB202190Y-27632. The colonic epithelium was washed with Advanced DMEM/F12 culture solution before seeding of the strain, and antibiotic-free DM was added thereto to produce a monolayer organoid co-culture system.

Figure 6A:
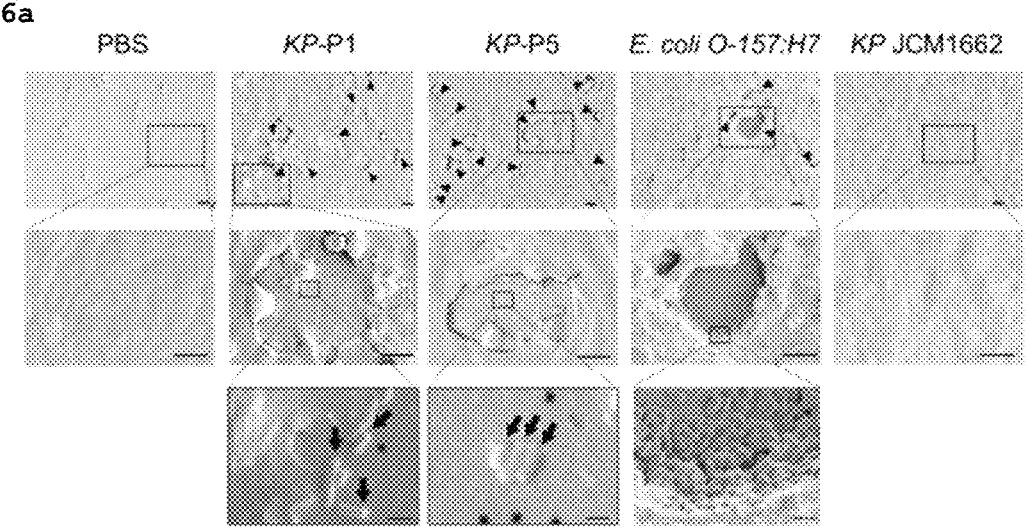
FIG. 6a includes scanning electron micrographs of large intestinal epithelia co-cultured, in a monolayer organoid co-culture system of the large intestine, with an enterohemorrhagic *Escherichia coli* strain 0-157:H7, a KP strain (KP JCM1662) not having an ability to form a pore on the large intestinal epithelium, and KP strains (KP-P1 and KP-P5) isolated from mesenteric lymph nodes of mice administered fecal sample derived from Psc/Uc. The scale bars indicate 20 μm.

(2) Co-Culture of Strain and Large Intestinal Epithelial Cell and Morphological Analysis KP strains (KP-P1 and KP-P5) isolated from the mesenteric lymph nodes of mice administered a fecal sample derived from Psc/Uc, enterohemorrhagic *Escherichia coli* O-157:H7, and a KP strain (KP JCM1662) obtained from Riken BioResource Research Center were added to the monolayer organoid co-culture systems each at a concentration of $1\times10^5$ CFU, followed by culturing for 8 hours. As a control, PBS was used. The co-cultured large intestinal epithelium was collected and pre-fixed in 5% glutaraldehyde (manufactured by TCI Chemicals) dissolved in PBS at 4° C. overnight. The pre-fixed sample was post-fixed in 1% osmium tetraoxide dissolved in PBS for 1 hour. The post-fixed sample was dehydrated with ethanol and coated by gold sputtering and was then observed with a scanning electron microscope ("VHX-D510 scanning electron microscope," manufactured by Keyence Corporation)" in a high-vacuum mode. The results are shown in FIG. 6a.

Figure 6B:
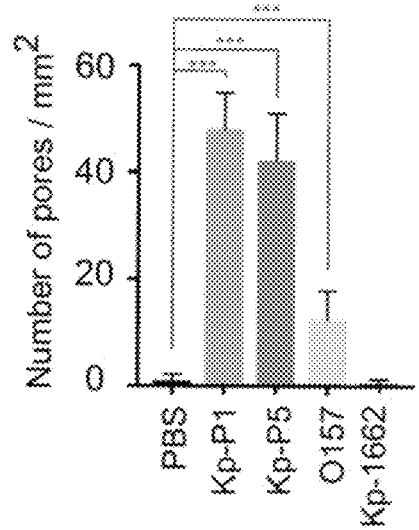
FIG. 6b is a graph showing the number of pores formed per unit area ($mm^2$) of each of the large intestinal epithelia.

In addition, the pores having a pore size of 10 µm or more on the large intestine were counted by observation of four independent positions of the large intestinal epithelium. The experiment was repeated 3 to 6 times. The results are shown in FIG. 6b. The results demonstrated that the KP strains (KP-P1 and KP-P5) of mice receiving a fecal sample derived from Psc/Uc formed pores on the large intestinal epithelium, but the JCM1662 strain formed no pores. In addition, a same test using other KP strains demonstrated that seven KP strains (JCM20034, ATCC BAA1705, ATCC BAA2552, ATCC700721, JCM20348, JCM20694, and JCM20507) formed pores on the large intestinal epithelium, but four strains (JCM1662, JCM1663, JCM1664, and ATCC700603) formed no pores on the large intestinal epithelium.

Figure 6C:
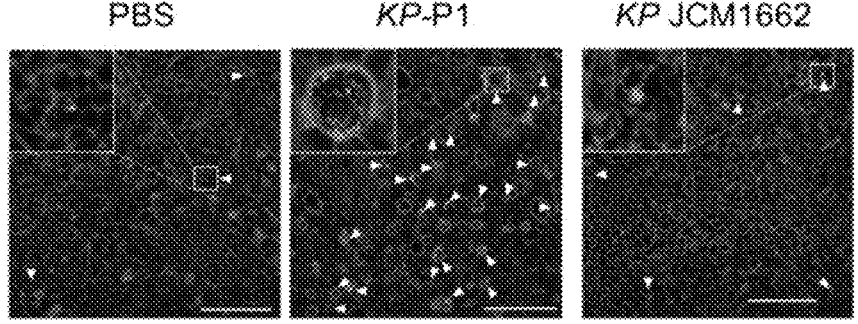
FIG. 6c includes fluorescence micrographs of the co-cultured large intestinal epithelia triple-stained with an anti-cleaved caspase-3 antibody, phalloidin, and Hoechst 33324. The scale bars indicate 100 μm.

Furthermore, the co-cultured large intestinal epithelial cells were triple-stained with an anti-cleaved caspase-3 antibody (manufactured by Cell Signaling Technology, Inc.), a filamentous actin stain phalloidin (manufactured by Thermo Fisher Scientific Inc.), and a DNA stain Hoechst 33324 (manufactured by Thermo Fisher Scientific Inc.), and apoptosis cells were observed with a confocal laser microscope (SP5, manufactured by Leica). The results are shown in FIG. 6c. It is inferred from the results that KP-P1 comes into direct contact with the large intestinal epithelium and induces apoptosis.

(3) Genome Sequencing of KP Strain

Figure 7:
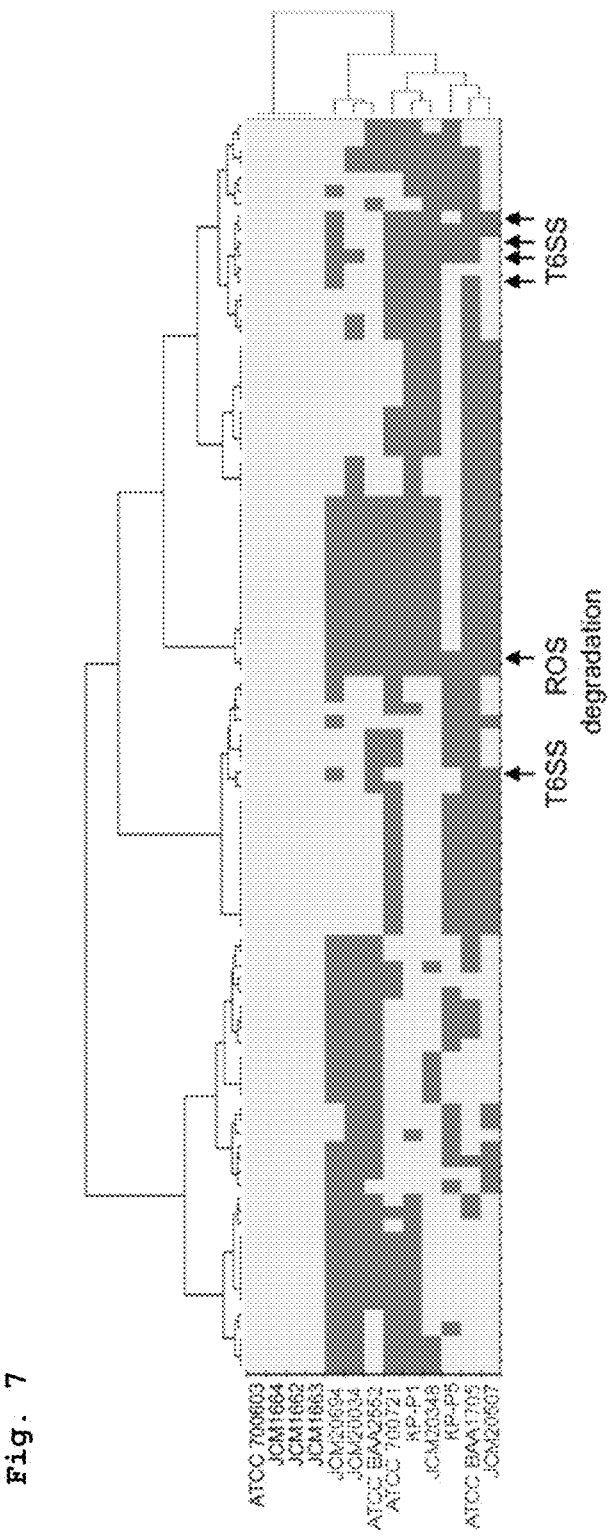
FIG. 7 is a chart showing the results of comparative analysis after whole genome sequencing of KP strains (ATCC 700603, JCM1664, JCM1662, and JCM1663) not having an ability to form a pore on the large intestinal epithelium and KP strains (JCM20694, JCM20034, JCM20348, ATCC BAA2552, ATCC 700721, KP-P1, KP-P5, ATCC BAA1705, and JCM20507) having an ability to form a pore on the large intestinal epithelium was performed.

The whole genome sequencing of the KP strain having or not having an ability to form a pore on the large intestinal epithelium was performed by whole-genome shotgun sequencing using PacBio RSII and Illumina MiSeq sequencers, and comparative analysis was performed. The results are shown in FIG. 7. The results demonstrated that in 97 orthologous genes, the KP strain having an ability to form a pore on the large intestinal epithelia includes genes involved in a type 6 secretion system (T6SS) and reactive oxygen species (ROS) decomposition.

Figure 8A:
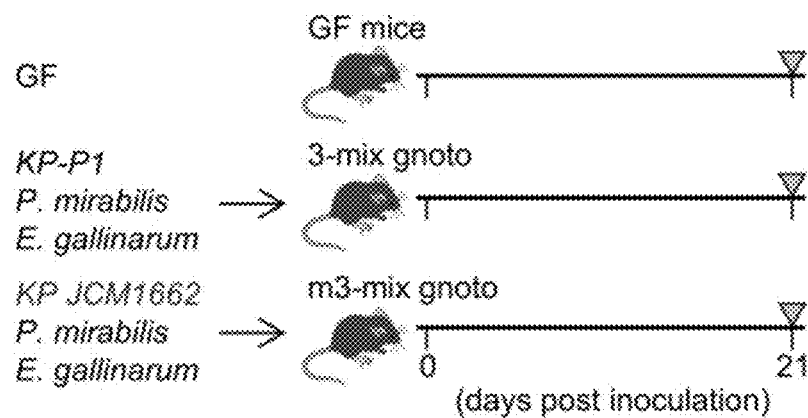
FIG. 8a is a schematic diagram illustrating an experimental scheme.
Figure 8B:
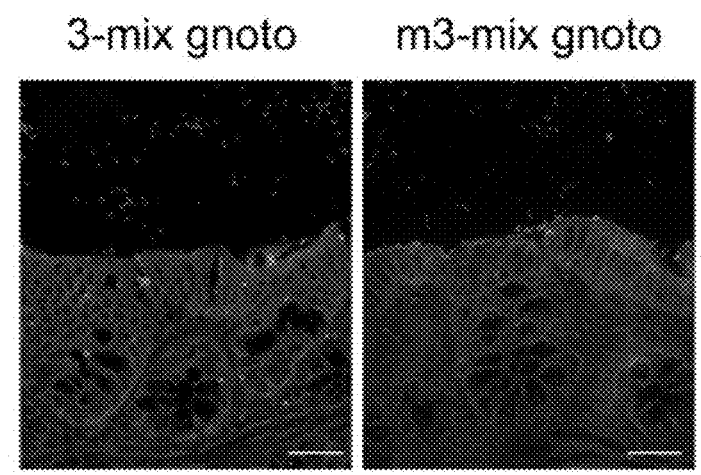
FIG. 8b includes fluorescence micrographs of the livers of a humanized gnotobiotic mouse (3-mix gnoto) prepared by administering KP-P1, PM, and EG to a GF mouse and of a humanized gnotobiotic mouse (m3-mix gnoto) prepared by administering JCM1662, PM, and EG to a mouse. The scale bars indicate 20 μm.

[Example 7] Evaluation 2 of Ability to Form a Pore on the Large Intestinal Epithelium of KP Stain (1) Histochemical Observation of Large Intestine Humanized gnotobiotic mice (3-mix gnoto) were produced by administering to GF mice three strains: PM, EG, and KP-P1 which is a KP strain forming pores on the large intestinal epithelia, and humanized gnotobiotic mice (m3-mix gnoto) were produced by administering to mice three strains: PM, EG, and KP JCM1662 which is a KP strain not forming pores on the large intestinal epithelia. On the 21st day from the administration, the ileum was collected from each mouse and was subjected to histochemical observation in the same manner as in Example 5 (2). The results are shown in FIG. 8b. The results demonstrated that 3-mix gnoto invaded the large intestine mucous membrane and the epithelial tissue, whereas m3-mix gnoto only slightly invaded the large intestine mucous membrane.

(2) Measurement of Serum LPS Level

Figure 8C:
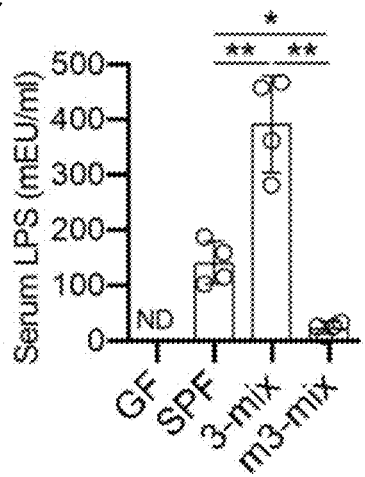
FIG. 8c is a graph showing the measurement results of serum lipopolysaccharide (LPS) of each mouse.

Blood was collected from GF mice, SPF mice, 3-mix gnoto, and m3-mix gnoto, and samples were prepared using ToxinSensor Chromogenic Limulus Amebocyte Lysate (LAL) Endotoxin Assay Kit (manufactured by GenScript Biotech Corporation) in accordance with the manual of the product. The absorbance at 540 nm was measured using FilterMax F3 Multi-Mode Microplate Reader (manufactured by Molecular Devices, LLC.) The results are shown in FIG. 8c. The results demonstrated that the serum LPS level in 3-mix significantly increased compared to those in the GF mice, SPF mice, and m3-mix groups.

(3) Evaluation of Induction of Th17 Cells

Figure 8D:
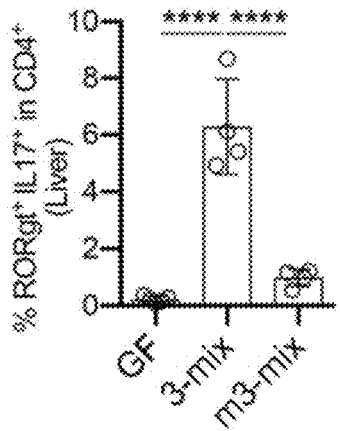
FIG. 8d is a graph showing the results of flow cytometric analysis of the cells in the liver of each mouse.

The livers of GF mice, 3-mix gnoto, and m3-mix gnoto were analyzed by flow cytometry using an anti-CD4 antibody (APC-cy7, BV510), an anti-IL-17 antibody, and an anti-RORγt antibody (manufactured by BD Pharmingen) in the same manner as in Example 2 (3). The results are shown in FIG. 8d. The results demonstrated that 3-mix gnoto significantly induced Th17 cells compared to GF mice and m3-mix gnoto.

Figure 9A:
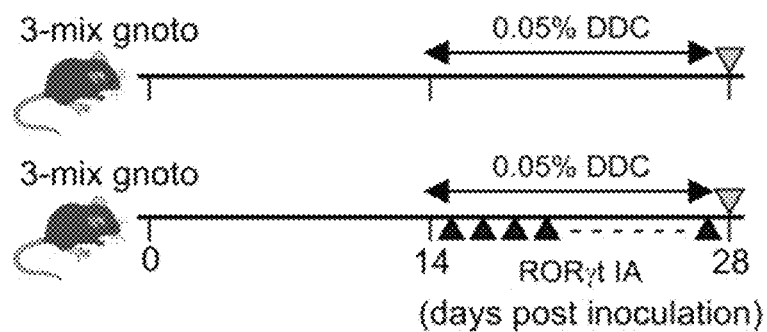
FIG. 9a is a schematic diagram illustrating an experimental scheme.
Figure 9B:
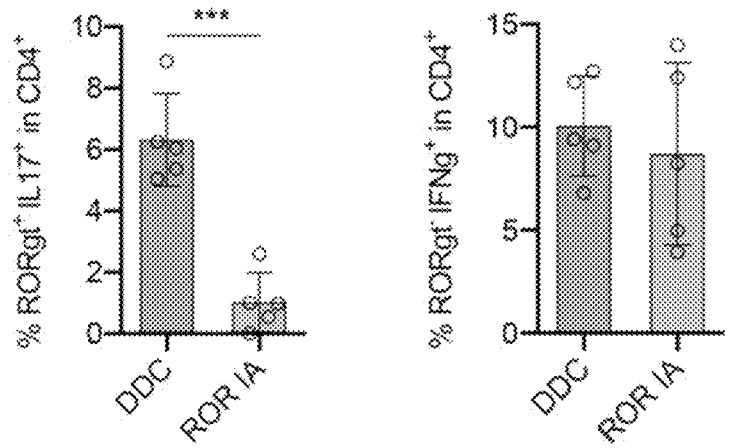
FIG. 9b includes graphs showing the results of flow cytometric analysis of the cells in the livers of humanized gnotobiotic mice (3-mix gnoto) treated with 3,5-dicarbetoxy-1,4-dihydrocollidine (DDC) and RORγt inverse agonist (RORIA) or water as a control.

[Example 8] Evaluation of Pathogenicity of KP Strain-Induced Th17 Cells (1) Evaluation of Induction of Th17 Cells by RORγt Inverse Agonist Treatment 3-mix gnoto was fed on a diet containing an RORγt inverse agonist (RORγt IA) or water as a control and DDC every day for 2 weeks 14 days after the administration of the strain (FIG. 9a). Subsequently, the liver of each mouse was subjected to flow cytometric analysis using an anti-CD4 antibody (APC-cy7, BV510), an anti-IL-17 antibody, an anti-IFN-γ antibody, and an anti-RORγt antibody (manufactured by BD Pharmingen) in the same manner as in Example 2 (3). The results are shown in FIG. 9b.

Figure 9C:
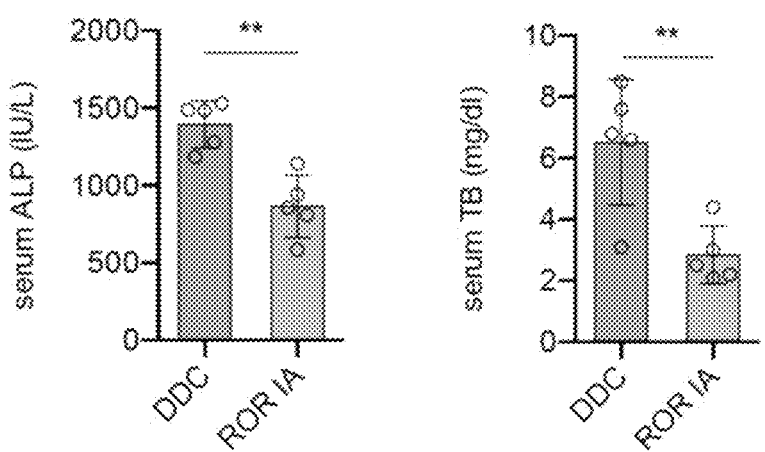
FIG. 9c includes graphs showing the measurement results of serum ALP (left) and serum TB (right) of the humanized gnotobiotic mice.
Figure 10:
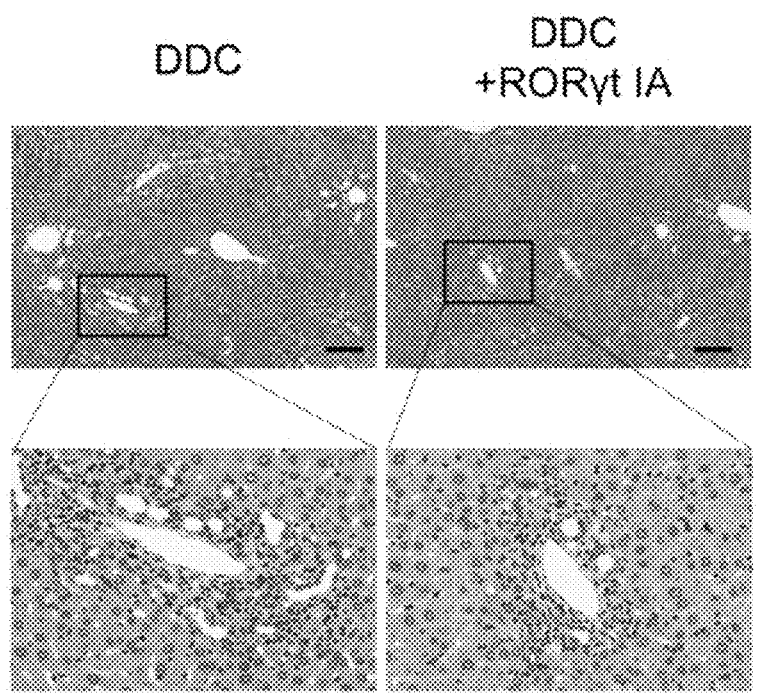
FIG. 10 includes micrographs of hematoxylin-eosin and Masson-trichrome stained liver sections of humanized gnotobiotic mice (3-mix gnoto) treated with DDC and RORIA. The scale bars indicate 100 μm.

In addition, serum alkaline phosphatase and serum total bilirubin were measured. The results are shown in FIG. 9c in the same manner as in Example 3 (1). Furthermore, sections of the liver were stained with hematoxylin-eosin and Masson-trichrome and were subjected to microscopic observation in the same manner as in Example 3 (2). The results are shown in FIG. 10.

It is inferred from these results that Th17 cells induced by strains in the liver play a pathogenetic role in the development of bile duct disorder induced by DDC.

The contents of Japanese Patent Application No. 2018-082192 (application date: Apr. 23, 2018), including the specification, claims, drawings, and abstract, are incorporated herein by reference in its entirety.

What is claimed is:

1. A method of identifying a microorganism that causes the development of primary sclerosing cholangitis in a subject, the method comprising
    culturing a fecal sample collected from the subject and counting the number of cells of the microorganism, wherein the microorganism is *Klebsiella pneumoniae*,
    determining the proportion of Th17 cells in a liver tissue obtained from the subject and correlating the number of cells of the *Klebsiella pneumoniae* in the fecal sample to the proportion of the Th17 cells in the liver tissue by Spearman rank-order correlation test,
    detecting and counting the number of pores formed per mm$^2$ unit area of a large intestinal epithelium tissue obtained from the subject using a scanning electron microscope, and
    wherein the presence of a correlation between the number of cells of the *Klebsiella pneumoniae* in the fecal sample of the subject and the proportion of the Th17 cells in the liver tissue of the subject combined with the formation of at least 40 pores with a pore size of 10 m or more per mm$^2$ unit area of the large intestinal epithelium tissue identifies the *Klebsiella pneumoniae* as the microorganism that causes the development of primary sclerosing cholangitis.

2. The method of claim 1, wherein the *Klebsiella pneumoniae* has type 6 secretion system (T6SS).

3. The method of claim 1, wherein the *Klebsiella pneumoniae* is the *Klebsiella pneumoniae* strain having the NITE deposit number BP-02879.

4. The method of claim 1, further comprising identifying additional microorganisms that cause the development of primary sclerosing cholangitis in the subject comprising
    culturing the fecal sample and counting the number of cells of the additional microorganisms, wherein the additional microorganisms are *Proteus mirabilis* and *Enterococcus gallinarum*,
    correlating the number of cells of the *Klebsiella pneumoniae*, the *Proteus mirabilis* and the *Enterococcus gallinarum* in the fecal sample to the proportion of the Th17 cells in the liver tissue by Spearman rank-order correlation test, and
    wherein the presence of a correlation between the number of cells of the *Klebsiella pneumoniae*, the number of cells of the *Proteus mirabilis*, and the number of cells of the *Enterococcus gallinarum* in the fecal sample of the subject and the proportion of the Th17 cells in the liver tissue of the subject combined with the formation of said pores in the large intestinal epithelium tissue identifies the *Klebsiella pneumoniae*, the *Proteus mirabilis*, and the *Enterococcus gallinarum* as the microorganisms that cause the development of primary sclerosing cholangitis.

5. The method of claim 4, wherein the *Proteus mirabilis* is the *Proteus mirabilis* strain having the NITE deposit number BP-02923 and the *Enterococcus gallinarum* is the *Enterococcus gallinarum* strain having the NITE deposit number BP-02922.

\* \* \* \* \*